United States Patent [19]

Armstrong

[11] 4,259,331
[45] Mar. 31, 1981

[54] OXYTETRACYCLINE COMPOSITIONS

[75] Inventor: William W. Armstrong, Mill Neck, N.Y.

[73] Assignee: Pfizer Inc., New York, N.Y.

[21] Appl. No.: 30,419

[22] Filed: Apr. 16, 1979

[51] Int. Cl.³ .................... A61K 31/65; A61K 31/79
[52] U.S. Cl. ....................................... 424/227; 424/80
[58] Field of Search ................................ 424/227, 80

[56] References Cited

U.S. PATENT DOCUMENTS

| | | | |
|---|---|---|---|
| 3,017,323 | 1/1962 | Gordon et al. | 424/227 |
| 3,557,280 | 1/1971 | Weber et al. | 424/227 |
| 3,929,989 | 12/1975 | Bergt | 424/227 |
| 4,018,889 | 4/1977 | Armstrong | 424/227 |

Primary Examiner—Jerome D. Goldberg
Attorney, Agent, or Firm—Francis X. Murphy; Charles J. Knuth; Allen J. Spiegel

[57] ABSTRACT

Pharmaceutical compositions containing magnesium-calcium-oxytetracycline mixed chelates in aqueous 2-pyrrolidone solution are disclosed.

7 Claims, No Drawings

OXYTETRACYCLINE COMPOSITIONS

BACKGROUND OF THE INVENTION

This invention relates to antibiotic compositions suitable for pharmaceutical use. More particularly, it relates to magnesium-calcium-oxytetracycline mixed chelates in aqueous 2-pyrrolidone solution.

U.S. Pat. No. 4,018,899 discloses oxytetracycline aqueous solutions containing 2-pyrrolidone as a cosolvent. The oxytetracycline is present as a magnesium chelate.

U.S. Pat. No. 3,017,323 discloses oxytetracycline in aqueous glycol solutions containing calcium and magnesium. A ratio of 1:1:3 of calcium:magnesium:oxytetracycline is employed.

U.S. Pat. No. 3,929,989 discloses suspensions of a calcium-magnesium-oxytetracycline complex having a molar ratio of combined calcium and magnesium to oxytetracycline of about 4 to 1 in aqueous 1,2-propanediol.

SUMMARY OF THE INVENTION

It has now been found that stable clear high potency solutions of oxytetracycline producing prolonged blood levels can be provided by means of a novel pharmaceutical composition comprising a solution in water of from about 20 to 30% w/v of oxytetracycline, from about 0.8 to 0.95 molar proportions based on said oxytetracycline of magnesium oxide, from about 0.15 to 0.3 molar proportions based on said oxytetracycline of a pharmaceutically acceptable calcium compound soluble in said solution and from about 40 to 60% w/v of 2-pyrrolidone, said composition having a pH value in the range of from about 7.5 to 9.5

DETAILED DESCRIPTION OF THE INVENTION

Oxytetracycline, the therapeutically-active component of this invention, is a widely used tetracycline-type antibiotic. It is particularly described in U.S. Pat. No. 2,516,081. An effective concentration range for oxytetracycline in the solutions of this invention is generally from about 20 to 30% w/v expressed as the free base. The preferred concentration is from about 20 to 25% w/v.

Magnesium ions and calcium ions combine with oxytetracycline in solution to form magnesium-calcium-oxytetracycline chelates. Magnesium oxide is the source of magnesium ions and is present in a concentration of from about 0.8 to 0.95 molar proportions based on said oxytetracycline. Calcium acetate is a convenient and preferred source of calcium ions, but other soluble, pharmaceutically acceptable calcium compounds may be employed such as calcium lactate and calcium propionate. The calcium compound is present in a concentration of from about 0.15 to 0.3 molar proportions based on said oxytetracycline.

2-Pyrrolidone is present as a co-solvent in a concentration of from about 40 to 60 percent w/v. The preferred concentration is from about 50 to 55% w/v. 2-Pyrrolidone is also known as 2-pyrrolidinone, 2-oxopyrrolidine, alpha-pyrrolidone and 2-ketopyrrolidine. It has an oral $LD_{50}$ of 8 g/kg in rats and 3.8 g/kg by intraperitoneal injection in mice. Its use allows for minimum volume per dose and excellent syringability due to the low viscosity of the resultant composition.

As an optional ingredient polyvinylpyrrolidone having a molecular weight of between about 5000 and 100,000 (K-12 to 30) may also be present in a concentration of from about 1 to 15% w/v. The polyvinylpyrrolidone preferred for this invention is one having an average molecular weight of about 10,000–17,000 (K-12 to 17). It is also present in part as a co-solublizer and may improve tissue toleration.

As optional co-solvents ingredients such as propylene glycol and glycerol formal may be present in concentrations of up to 15% w/v.

The stability of these solutions for therapeutic administration is still further enhanced by the use of anti-oxidants such as sodium or magnesium formaldehyde sulfoxylate and monothioglycerol at levels of from about 0.01 to 1% w/v.

The pH value is adjusted if necessary to pH 7.5 to 9.5. The preferred range is pH 8.5 to 9.0. The pH can be adjusted with organic bases such as monoethanolamine, dimethylaminoethanol, dimethylamine and so forth. Of these compounds, monoethanolamine is the preferred compound.

The compositions of this invention are readily prepared by mixing and dissolving the calcium compound in a portion of the water. The 2-pyrrolidone is then mixed with the major portion of the water and polyvinylpyrrolidone, if present in the formulation, is added and dissolved. The solution is heated to 45°–75° C. and the antioxidants added with stirring. The magnesium oxide is slurried with this solution and the oxytetracycline is slowly added with stirring until solution is obtained. The calcium compound in solution is then slowly added to the magnesium oxytetracycline solution with stirring until a clear solution is formed. After the solution cools to room temperature the pH is adjusted if necessary.

Solution is then brought up to volume with water.

These compositions are easy to syringe over a wide temperature range, have acceptable animal tissue toleration and give therapeutic blood levels for a period for up to 15 days. The mixed magnesium-calcium chelate produces on injection a controlled amount of precipitated antibiotic which acts as a depot and brings about unusually prolonged blood levels which are not obtained with the use of the magnesium chelate alone.

EXAMPLE 1

|  | gm./100ml. |
|---|---|
| Oxytetracycline (based on a potency of 927 mcg./mg. plus a 2% overage) | 27.51 |
| Magnesium oxide | 1.844 |
| Calcium acetate | 1.931 |
| 2-pyrrolidone | 50.00 |
| Polyvinylpyrrolidone, K-17 | 5.00 |
| Sodium formaldehyde sulfoxylate | 0.30 |
| Monoethanolamine, to adjust pH to 8.5 | |
| Water q.s. to | 100 ml. |

The calcium acetate was dissolved in 10 ml. of water. The 2-pyrrolidone was mixed with 30 ml. of water. The polyvinylpyrrolidone was added and dissolved. The solution was heated to 45° C. and the sodium formaldehyde sulfoxylate was added and dissolved with stirring. The magnesium oxide was then slurried with the solution. The oxytetracycline was slowly added with stirring until solution was attained. The calcium acetate solution was slowly added to the magnesiumoxytetracycline solution with stirring until a clear solution is formed. The solution was then allowed to cool to room temperature and the pH adjusted to 8.5 with monoethanolamine. The solution was then brought up to volume with water.

The above solution containing 250 mg./ml. of oxytetracycline activity had a viscosity of 45 cts. at 25° C.

EXAMPLE 2

The following solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 1.931 |
| 2-pyrrolidone | 55.00 |
| Sodium formaldehyde sulfoxylate | 0.30 |
| Monoethanolamine, to adjust pH to 8.5 | |
| water q.s. to | 100 ml. |

The viscosity was 49 cts at 25° C.

EXAMPLE 3

The following solution containing 300 mg./ml. of oxytetracycline activity was prepared using the procedure described in Example 1.

|  | gm./100ml. |
|---|---|
| Oxytetracycline (based on a potency of 927 mcg./mg. plus a 2% overage) | 33.00 |
| Magnesium oxide | 2.221 |
| Calcium acetate | 2.111 |
| 2-Pyrrolidone | 50.00 |
| Polyvinylpyrrolidone, K-17 | 3.00 |
| Sodium formaldehyde sulfoxylate | 0.30 |
| Monoethanolamine, to adjust pH to 8.5 | |
| water q.s. to | 100 ml. |

The viscosity was 173 cts. at 25° C.

EXAMPLE 4

The following solution containing 300 mg./ml. of oxytetracycline activity was prepared using the procedure described in Example 1.

|  | gm./100ml. |
|---|---|
| Oxytetracycline (based on a potency of 927 mcg./mg. plus a 2% overage) | 33.00 |
| Magnesium oxide | 2.221 |
| Calcium acetate | 2.111 |
| 2-Pyrrolidone | 55.00 |
| Sodium formaldehyde sulfoxylate | 0.30 |
| Monoethanolamine, to adjust pH to 8.5 | |
| water q.s. to | 100 ml. |

The viscosity was 138 cts. at 25° C.

EXAMPLE 5

A solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 1.931 |
| 2-Pyrrolidone | 50.00 |
| Polyvinylpyrrolidone, K-17 | 3.00 |
| Sodium formaldehyde sulfoxylate | 0.30 |
| Monoethanolamine, to adjust pH to 8.5 | |
| water q.s. to | 100 ml. |

The viscosity was 69 cts. at 25° C.

EXAMPLE 6

The following solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 3.379 |
| 2-Pyrrolidone | 50.00 |
| Polyvinylpyrrolidone, K-17 | 3.00 |
| Sodium formaldehyde sulfoxylate | 0.30 |
| Monoethanolamine, to adjust pH to 8.5 | |
| water q.s. to | 100 ml. |

The viscosity was 72 cts. at 25° C.

EXAMPLE 7

The following solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 2.075 |
| Calcium acetate | 1.931 |
| 2-Pyrrolidone | 50.00 |
| Polyvinylpyrrolidone, K-17 | 3.00 |
| Sodium formaldehyde sulfoxylate | 0.30 |
| Monoethanolamine, to adjust pH to 8.5 | |
| water q.s. to | 100 ml. |

The viscosity was 58 cts. at 25° C.

EXAMPLE 8

The following solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 3.379 |
| 2-Pyrrolidone | 50.00 |
| Polyvinylpyrrolidone, K-12 | 5.00 |
| Sodium formaldehyde sulfoxylate | 0.30 |
| Monoethanolamine, to adjust pH to 8.5 | |
| water q.s. to | 100 ml. |

The viscosity was 75 cts. at 25° C.

EXAMPLE 9

The following solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 2.897 |
| 2-Pyrrolidone | 5.00 |
| Polyvinylpyrrolidone, K-12 | 7.50 |
| Sodium formaldehyde sulfoxylate | 0.30 |
| Monoethanolamine, to adjust pH to 8.5 |  |
| water q.s. to | 100 ml. |

The viscosity was 115 cts. at 25° C.

EXAMPLE 10

The following solution containing 250 mg./ml. of oxytetracycline activity was prepared using the procedure described in Example 1, except that the glycerol formal was added to the 2-pyrrolidone before the addition of water.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 2.897 |
| 2-Pyrrolidone | 5.00 |
| Polyvinylpyrrolidone, K-12 | 7.50 |
| Glycerol formal | 15.00 |
| Sodium formaldehyde sulfoxylate | 0.50 |
| Monoethanolamine, to adjust pH to 8.5 |  |
| water q.s. to | 100 ml. |

The viscosity was 138 cts. at 25° C.

EXAMPLE 11

The following solution containing 250 mg./ml. of oxytetracycline activity was prepared using the procedure described in Example 1.

|  | gm./100ml. |
|---|---|
| Oxytetracycline (based on a potency of 927 mcg./mg. plus a 2% overage) | 22.008 |
| Magnesium oxide | 1.844 |
| Calcium acetate | 2.897 |
| 2-Pyrrolidone | 55.00 |
| Polyvinylpyrrolidone, K-12 | 10.00 |
| Sodium formaldehyde sulfoxylate | 0.30 |
| Monoethanolamine, to adjust pH to 8.0 |  |
| water q.s. to | 100 ml. |

The viscosity was 84 cts. at 25° C.

EXAMPLE 12

The following solution containing 250 mg./ml. of oxytetracycline activity was prepared using the procedure described in Example 8.

|  | gm./100ml. |
|---|---|
| Oxytetracycline (based on a potency of 927 mcg./mg. plus a 2% overage) | 22.008 |
| Magnesium oxide | 1.844 |
| Calcium acetate | 2.897 |
| 2-Pyrrolidone | 50.00 |
| Polyvinylpyrrolidone, K-12 | 7.50 |
| Glycerol formal | 15.0 |
| Sodium formaldehyde sulfoxylate | 0.30 |
| Monoethanolamine, to adjust pH to 8.5 |  |
| water q.s. to | 100 ml. |

The viscosity was 83 cts. at 25° C.

EXAMPLE 13

The following solution containing 250 m.g./ml. of oxytetracycline activity was prepared using the procedure described in Example 1.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 1.931 |
| 2-Pyrrolidone | 50.00 |
| Polyvinylpyrrolidone, K-17 | 3.00 |
| Sodium formaldehyde sulfoxylate | 0.30 |
| Monothioglycerol | 1.00 |
| water q.s. to | 100 ml. |

The viscosity was 45 cts. at 25° C.

EXAMPLE 14

The following solution containing 250 mg./ml. of oxytetracycline activity was prepared using the procedure described in Example 8, except that propylene glycol is used instead of glycerol formal.

|  | gm./100ml. |
|---|---|
| Oxytetracycline (based on a potency of 927 mcg./mg. plus a 2% overage) | 27.51 |
| Magnesium oxide | 1.844 |
| Calcium acetate | 2.897 |
| 2-Pyrrolidone | 50.00 |
| Polyvinylpyrrolidone, K-12 | 7.50 |
| Propylene glycol | 15.00 |
| Sodium formaldehyde sulfoxylate | 0.50 |
| Monoethanolamine, to adjust pH to 8.5 |  |
| water q.s. to | 100 ml. |

The viscosity was 135 cts. at 25° C.

EXAMPLE 15

A mixed magnesium-calcium-oxytetracycline chelate solution and a magnesium-oxytetracycline chelate solution were each administered intramuscularly to cattle at two sites on the same leg at a dosage level of 30 mg. oxytetracycline/kg. Blood samples were taken at the indicated time intervals and plasma oxytetracycline levels were determined.

|  | mcg./ml. oxytetracycline Post Injection | | | | | | |
|---|---|---|---|---|---|---|---|
|  | 4 Hrs. | 1 Days | 4 Days | 7 Days | 10 Days | 13 Days | 15 Days |
| Magnesium-calcium chelate (Ex. 6) | 1.72 | 1.30 | 0.38 | 0.35 | 0.31 | 0.26 | 0.23 |
| Magnesium-chelate (Ex. 1 of U.S. Pat. No. 4,018,889) | 5.07 | 2.27 | 0.27 | 0.20 | 0 | 0 | 0 |

The above results clearly illustrate the prolonged blood levels achievable with the mixed chelate formulation.

I claim:

1. An aqueous oxytetracycline composition comprising from about 20 to 30% w/v of oxytetracycline, from about 40 to 60% of 2-pyrrolidone, from about 0.8 to 0.95 molar proportions of magnesium oxide based on said oxytetracycline and from about 0.15 to 0.3 molar proportions based on said oxytetracycline of a pharmaceutically acceptable calcium compound soluble in said composition, said composition having a pH value in the range of from about 7.5 to 9.5.

2. A composition as claimed in claim 1 wherein said oxytetracycline is present at a level of from about 20 to 25% w/v.

3. A composition as claimed in claim 1 wherein said calcium compound is introduced in the form of calcium acetate.

4. A composition as claimed in claim 1 wherein polyvinylpyrrolidone having an average molecular weight of between about 5,000 and 100,000 is also present in a concentration of from about 1 to 15% w/v.

5. A composition as claimed in claim 1 wherein glycerol formal or propylene glycol is also present in a concentration of from about 1 to 15% w/v.

6. A composition as claimed in claim 1 wherein said 2-pyrrolidone is present in a concentration of from about 50 to 55% w/v.

7. An oxytetracycline composition comprising a solution in water of from about 20 to 25% w/v of oxytetracycline, from about 0.8 to 0.95 molar proportions based on said oxytetracycline of magnesium oxide, from about 0.15 to 0.3 molar proportions based on said oxytetracycline of calcium acetate, from about 50 to 55% w/v of 2-pyrrolidone and from about 1 to 15% w/v of polyvinylpyrrolidone having an average molecular weight of about 10,000 to 17,000, said composition having a pH value in the range of from about 8.5 to 9.

* * * * *